(12) United States Patent
Hell et al.

(10) Patent No.: US 6,292,538 B1
(45) Date of Patent: Sep. 18, 2001

(54) X-RAY TUBE WITH FLYING FOCUS

(75) Inventors: Erich Hell; Detlef Mattern, both of Erlangen; Peter Schardt, Hoechstadt, all of (DE)

(73) Assignee: Siemens Aktiengesellschaft, Munich (DE)

( * ) Notice: Subject to any disclaimer, the term of this patent is extended or adjusted under 35 U.S.C. 154(b) by 0 days.

(21) Appl. No.: 09/487,281

(22) Filed: Jan. 19, 2000

(30) Foreign Application Priority Data

Feb. 1, 1999 (DE) .............................................. 199 03 872

(51) Int. Cl.[7] .................................................. H01J 35/30
(52) U.S. Cl. ............................................. 378/137; 378/138
(58) Field of Search .................................... 378/137, 136, 378/119, 125, 121, 145

(56) References Cited

U.S. PATENT DOCUMENTS

| 4,748,650 | * | 5/1988 | Ammann | 378/137 |
| 5,528,658 | * | 6/1996 | Hell | 378/137 |
| 5,751,784 | * | 5/1998 | Enck | 378/140 |
| 5,812,632 | * | 9/1998 | Schardt et al. | 378/137 |
| 5,822,395 | * | 10/1998 | Schardt et al. | 378/137 |
| 5,883,936 | | 3/1999 | Hell et al. | 378/125 |
| 6,091,799 | * | 7/2000 | Schmidt | 378/137 |
| 6,181,771 | * | 1/2000 | Hell et al. | 378/137 |

* cited by examiner

*Primary Examiner*—Robert H. Kim
*Assistant Examiner*—Irakli Kiknadze
(74) *Attorney, Agent, or Firm*—Schiff Hardin & Waite

(57) ABSTRACT

X-ray tube with flying focus has a magnet system for deflecting and focusing the electron beam, whereby the magnet system including a carrier that is constructed as an iron yoke and that has four pole projections that are arranged around the axis of the electron beam offset from one another by 90°, on which two pairs of coils (z-coils and φ-coils) are arranged so as to be offset from one another 90°. The individual coils of each pair supplied with a common high-frequency alternating current that deflects the electron beam in the φ-and z-directions, respectively, in a pulsed manner.

7 Claims, 3 Drawing Sheets

X-RAY TUBE WITH FLYING FOCUS

BACKGROUND OF THE INVENTION

1. Field of the Invention

The present invention relates to an X-ray tube of the type having a vacuum housing in which a cathode and an anode are arranged, wherein the cathode emits electrons forming a beam and the electrons are accelerated by an electrical field, so as to strike the anode, at a focus (focal spot) and having a magnet system for deflecting and focusing the electron beam formed by several coil elements with current flowing therein, so as to produce a flying focus on the anode from which X-rays emanate.

2. Description of the Prior Art

In computed tomography with a single-line detector, the electron beam of the X-ray tube can be deflected in the $\phi$-direction, i.e. in the direction of the perimeter of the outer annular margin of the anode (known as a flying focus), for improving the resolution. This is achieved by a magnet system whose dipole field deflects the beam at high speed. Varying focal spot positions are thus obtained, and the number of projections thus can be increased.

For future application with a multi-line detector and/or surface detector, it would be desirable to simultaneously displace the focal spot in the z direction in order to achieve an enhancement of the resolution in spiral scans.

To achieve these different flying focusings, magnet systems that are spatially separated in the z-direction, which corresponds to the direction parallel to the longitudinal axis of the x-ray tube, can be used, but this increases the length of the tube appreciably, which in turn causes problems in the focusing. Therefore, such a design is extremely undesirable in computed tomography.

SUMMARY OF THE INVENTION

It is an object of the present invention to provide an X-ray tube of the type described above wherein a flying focus deflection of the electron beam is possible in both the $\phi$ and z directions, with a compact structure and with simple control.

This object is inventively achieved in an X-ray tube of the type described above wherein the magnet system has a carrier constructed as a yoke, preferably an iron yoke, and which has four pole projections that are arranged at an angular offset to one another, preferably an offset of 90°, two of which are arranged opposite one another, preferably in one plane. The coils of two coil pairs, for instance z coils and $\phi$ coils, (of a cylindrical (r, $\phi$, z) coordinate system) which are preferably offset by 90° to one another, are arranged on the carrier, with the coils of a pair being arranged opposite one another between different pole projections. The coils of each pair are energized by a common current, preferably a high-frequency alternating current that deflects the electron beam in a pulsing manner, so that the electron beam can be deflected by one pair of coils in a first direction, for instance the z-direction, that is different from a second direction, for instance the $\phi$-direction, in which the electron beam can be deflected by the other pair of coils.

The inventive construction in which the coils of the pairs, for instance z coils and $\phi$-coils, are arranged on the carrier, which is preferably constructed as a closed yoke, results in a rather compact realization of the magnet system for the flying focus deflection of the electron beam.

In X-ray tubes having a centrally arranged cathode in which the electron beam must be deflected from the center axis of the tube onto the radially outer margin or edge region of the anode, as is the case in basically all rotary-piston tubes, r-coils that are connected to a separate current supply should be provided in addition to the aforementioned z-coils. These r-coils are supplied with a constant current in order to deflect the beam onto the desired path of the edge region of the anode. The z-coils and r-coils do not differ in their basic construction apart from the fact that they must be laid out for alternating current in some cases and for direct current in others. The deflection of the electron beam they respectively cause is in the same direction. For the r-coils this is primarily a radially fixed deflection of the electron beam onto the outer edge of the anode; for the z-coils the deflection modifies the focal spot in the z-direction, which can be functionally realized only by pulsing the beam in the re-direction. Due to the beveled edge region of the anode, this radial displacement simultaneously produces an axial change of location of the focal spot in the z-direction.

Specifically in rotary-piston tubes, due to the deflection of the electron beam by the r-coils onto the edge region of the anode, an other possibility is needed for shaping the focal spot, for which purpose a quadrupolar system is particularly suitable. In an embodiment of the invention, the magnet system can be as described in German OS 196 31 899. This quadrupolar magnet system utilizes the same carrier as is set forth in the present invention for realizing a flying focus, this being constructed as an iron yoke, whereby the four q-coils (quadrupole coils) for generating the quadrupole field are preferably arranged on the pole projections.

In this embodiment it is possible to arrange only four coils on the pole projections, which are selectively driven as q-coils, z-coils and r-coils by simultaneously using three different current supply systems which respectively supply the corresponding deflection currents to the drive coils. Driving the same coils with different currents, that is, in part with direct currents of high amplitude and in part with high-frequency alternating currents of low amplitude, entails a considerable wiring outlay, however, so that nevertheless it is simpler and less expensive to provide separate coil systems for each magnetic field, which are individually driven completely independently from each other.

DESCRIPTION OF THE PREFERRED EMBODIMENTS

Figure 1:
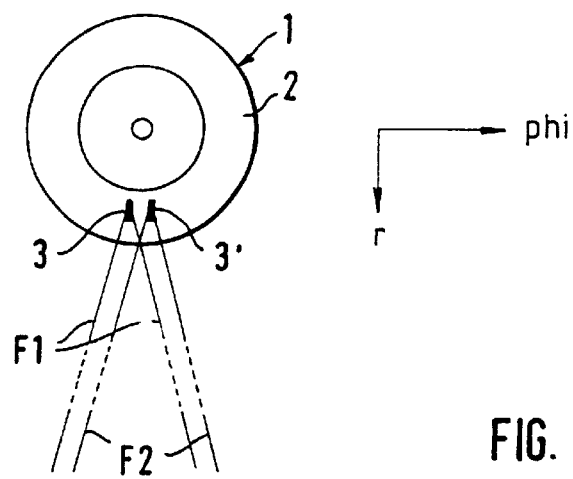
FIG. 1 is a plan view of an anode with flying focusing of the electron beam in the $\phi$-direction, suitable for use in the inventive X-ray tube.

FIG. 1 shows a plan view of an anode 1 with a beveled edge region 2. An electron beam (which is not illustrated) is deflected onto this edge region 2 and forms a focal spot 3. The magnet system for generating and deflecting the electron beam is constructed so that a high-frequency dipole field is superimposed thereon, which causes the focal spot to skip from the position 3 into the position 3' and back again at high speed. An additional high-frequency deflection in the φ-direction is thus accomplished. By this flying focus, as it is called, the resolution is improved in computed tomography with single-line detectors. When the images are displaced by approximately one-half pixel by the skipping of the focal spot in the φ-direction, the resolution is twice as high with this technique as without the flying focus.

Figure 2:
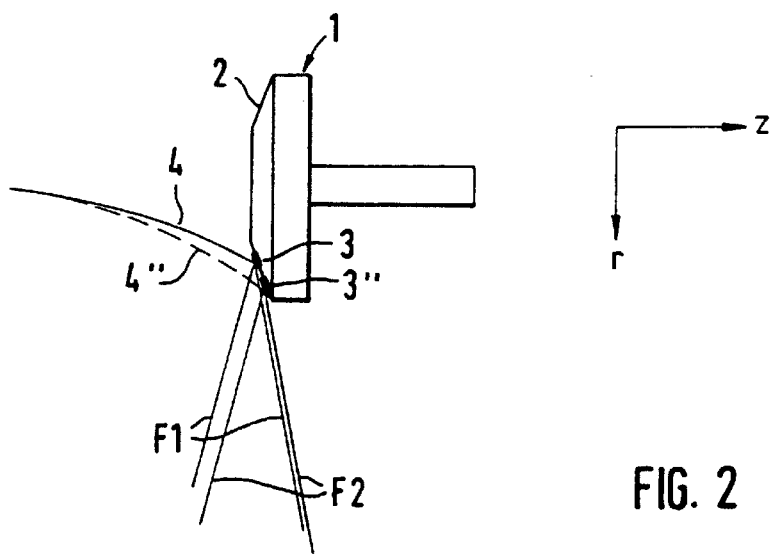
FIG. 2 is a side view of the anode having flying focusing in the z-direction, which is provided with a beveled plate margin, suitable for use in the inventive X-ray tube.

For future applications with a multiline detector and/or surface detector, it is expedient to also displace the focal spot in the z-direction at the same time, in order to achieve an improvement of the resolution in spiral scans, which is illustrated in FIG. 2. The electron beam 4 can be seen, which can also be deflected into the position 4' by a corresponding bipolar field, so that the focal spot 3" appears instead of the focal spot 3. This deflection is first accomplished in the r-direction, that is, along an anode radius in an outward direction. But there is also necessarily a shift in the z-direction, that is, in the direction of the longitudinal axis of the x-ray tube, along the angled direction of the edge margin 2, which is inclined about 8° in computed tomography. Since the present case involves only the high-frequency z-component of the shift and not the normal static defection of the electron beam from the cathode onto the edge region 2 of the anode, in order to distinguish the deflections that ensue differently and that serve different purposes, the high-frequency wobble frequency of the focal spot between the positions 3 and 3" is referred to a shift in the z-direction, whereas the static deflection of the electron beam that is superimposed with the wobble shift is referred to as deflection in the r-direction.

Figure 3:
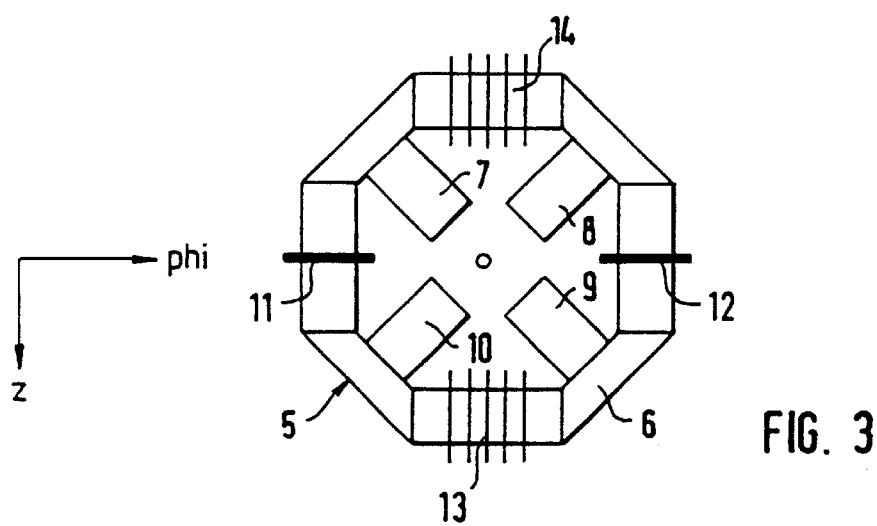
FIG. 3 schematically illustrates a magnet system for simultaneous flying focus in the $\phi$- and z-directions, in accordance with the invention.
Figure 4:
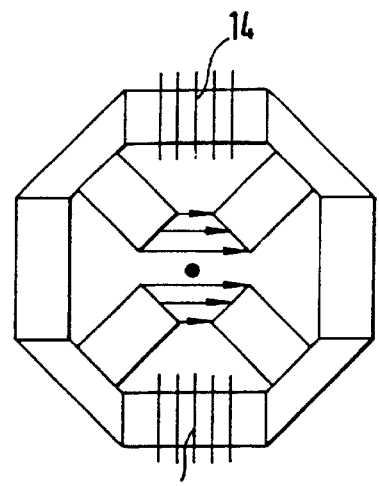
FIGS. 4 and 5 respectively show the field patterns of the z-coils and the $\phi$-coils of the magnet system as illustrated in FIG. 3, shown separately.

FIG. 3 depicts the arrangement of the magnet system at the X-ray tube as well as the definition of the coordinates φ and z. The magnet system includes a carrier 5 that is constructed as an iron yoke and that is formed by a yoke 6 and pole projections 7, 8, 9 and 10 that project therefrom, which are offset from one another 90°. The coils 11 and 12 deflect the electron beam in the φ-direction, and coils 13 and 14 deflect the electron beam in the z-direction. The characteristic patterns of the respective fields that are generated by these coil systems 11, 12, and 13, 14 between the ends of the pole projections are illustrated in FIG. 4. It should be noted that in FIG. 4, again, for the z-deflection, the field of the coils 13 and 14 effectuate the rapid high-frequency deflection of the electron beam in the r-direction, which in turn brings about a shifting of the focal spot in the z-direction along the angled direction of the edge region.

Figure 5:
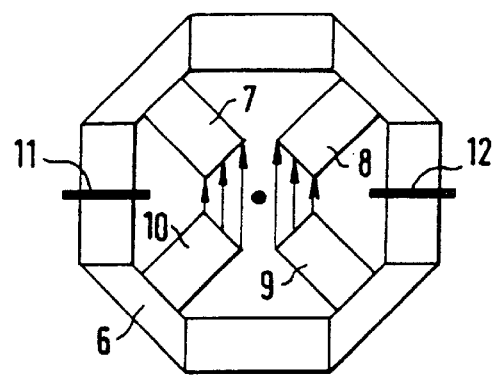

The flying focus requires a deflection in the φ-direction. The dipole field required for this is generated by the φ-coils, the effect of which is again shown in detail in FIG. 5. These coils need to generate only a small magnetic field amplitude and can be realized by only a few windings. The demand for low inductivity and high edge steepness can thus be satisfied.

Figure 8:
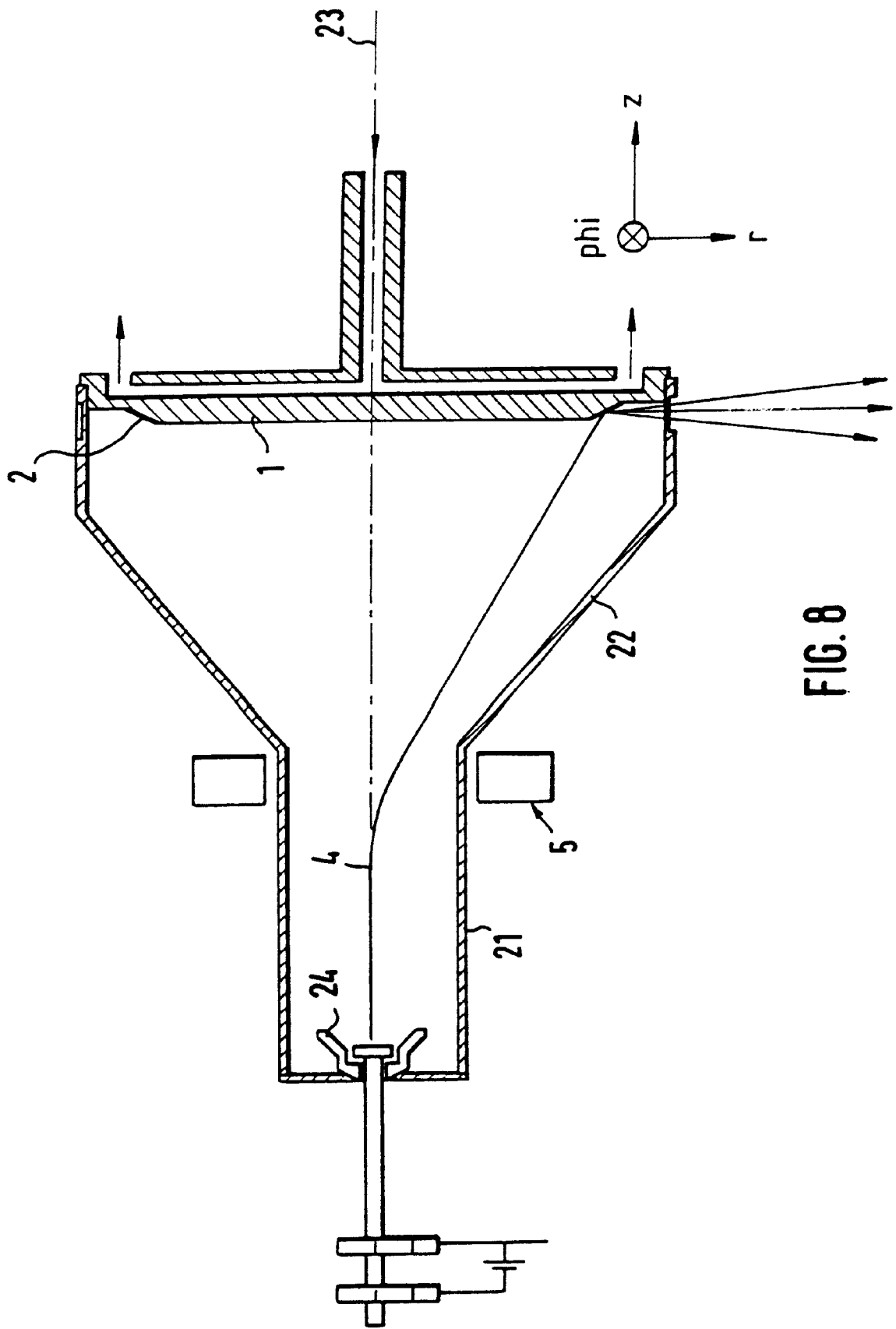
FIG. 8 is a schematic section through an inventive rotary-piston tube with its magnet system.

A rotary-piston X-ray radiator for computed tomography as illustrated sectionally and schematically in FIG. 8 requires a magnet system that must perform three functional objects with different requirements and conditions:

1. Deflection of the electron beam in the r-direction onto the focal path. This quasi-stationary deflection has a very high time constant, and a large high-voltage-dependent amplitude is necessary.

2. This deflection of the beam in the r-direction must be superimposed with an additional high-frequency deflection of the beam in the r-direction in order to produce the focal spot displacement in the z-direction. Basically, this could be accomplished by driving the r-coils with two different current supply systems at the same time, one of which is a direct current system that generates the radial deflection, and the other of which is a high-frequency current system that superimposes a high-frequency wobble voltage with which the focal spot displacement in z-direction is produced.

3. Generation of the line focus, that is, of the correct relation of length to width of the focal spot. This is accomplished with a very high time constant, that is, also practically stationary, and a small amplitude dependency on the high-voltage on the high-voltage is required in the magnetic field. The line focus can be produced by a quadrupolar field, as detailed below.

4. Deflection of the focal spot in the φ-direction for the flying focus. This magnet system has a very low time constant, that is, a high frequency and a small electronically controlled amplitude.

Figure 6:
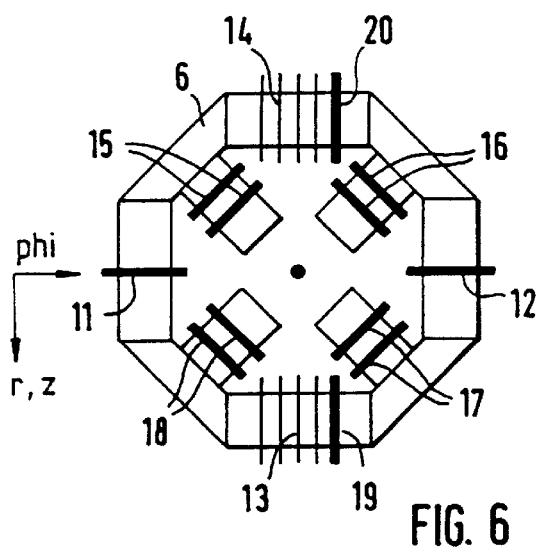
FIG. 6 shows the construction of an inventive flying focus magnet system for a rotary-piston tube.
Figure 7:
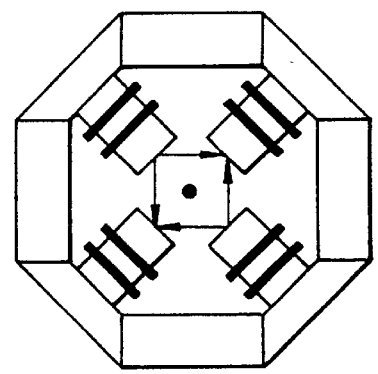
FIG. 7 illustrates the quadrupole field generated by the q-coils in FIG. 6.

A magnet system that satisfies all these requirements can have the construction illustrated in FIG. 6 and utilizes ten individual coils in the preferred embodiment, two coils being interconnected for the r deflection, two coils being interconnected for the φ-deflection and two coils interconnected for the z-deflection, and four coils being interconnected for the focusing. The four q coils 15 to 18 are arranged on the pole projections and are driven so as to generate a quadrupole field as illustrated in FIG. 7. This quadrupole field effectuates the shaping of the line focal spot by spreading it in one direction and contracting it proportionately in the other direction.

The r-coils 19 and 20 that are arranged directly next to the z-coils 13 and 14 on the closed yoke of the carrier 6 may be formed by one common coil, as has already been mentioned. It is advantageous to split these into separate coils 13, 14 for displacing the focal spot in the z-direction and coils 19, 20 for the purely static deflection of the electron beam onto the edge region 2 of the anode 1 so that the current supply systems can be realized much more easily. This is because, when a single coil is used for the r-field and, for instance, the high-frequency z-field, conflicting requirements must then be satisfied, and it is not possible to lay out the coil as would be most expedient for the respective deflections. Furthermore, problems arise due to feedback into the different current generating systems. From a purely theoretical standpoint and in consideration of all the described disadvantages in the current control, it would be possible to construct the magnet system using the coils 15 to 18 only, which would then have to be driven with four current supply systems, respectively, in order to generate the quadrupole field, the field for the φ-deflection, that for the r-deflection, and that for the high-frequency z-deflection. FIG. 8 schematically illustrates how an inventive magnet system with the carrier 5 is arranged in the region of the throat 21 of the vacuum housing 22 of a rotary-piston tube in order to shape the electron beam 4 emanating from the cathode 24, that is arranged centrally on the axis of rotation 23 and in order to deflect it onto the edge region 2 of the anode 1. By constructing the magnet system on the carrier 5 according to FIG. 6, it is then possible to additionally achieve the focus that oscillates back and forth in four directions and the additional displacement of the focal spot in the z-direction, besides the static r-deflection of the electron beam onto the edge region 2 and the snaping of the focal spot by means of the quadrupole field.

Although modifications and changes may be suggested by those skilled in the art, it is the intention of the inventors to embody within the patent warranted hereon all changes and modifications as reasonably and properly come within the scope of their contribution to the art.

We claim as our invention:

1. An X-ray tube comprising:

a vacuum housing;

a cathode and an anode disposed in said vacuum housing, said cathode emitting electrons which strike said anode to produce X-rays;

a magnet system disposed between said cathode and said anode through which said electrons pass for deflecting and focusing said electrons to produce a flying focal spot on said anode; and said magnet system comprising a yoke through which said electrons pass having four pole projections which are angularly offset relative to each other and which are arranged in pairs, with two pole projections in each pair being disposed opposite each other, four coils wound around said yoke and being respectively disposed between neighboring pole projections, said coils comprising a first pair and a second pair with the coils in each of said first and second pairs being disposed opposite each other, said first pair of coils being supplied with a first common current and said second pair of coils being supplied with a second common current so that said electrons are deflected by said first pair of coils in a first direction, and said electrons are deflected by said second pair of coils in a second direction which is different from said first direction.

2. An X-ray tube as claimed in claim 1 wherein said pole projections are successively offset from each other by 90°, and wherein said coils are successively offset from each other by 90°, and wherein said first pair of coils comprises z-coils for deflecting said electrons in a z-direction of a cylindrical coordinate system, and wherein said second pair of coils comprises φ-coils for deflecting said electron beam in a φ-direction of said cylindrical coordinate system.

3. An X-ray tube as claimed in claim 1 wherein at least one of said first common current and said second common current comprises a high-frequency alternating current that deflects said electrons in a pulsed manner.

4. An X-ray tube as claimed in claim 1 wherein said yoke comprises a closed yoke.

5. An X-ray tube as claimed in claim 1 wherein said anode has an annular edge region, and wherein said magnet system further comprises r-coils for deflecting said electrons onto said edge region in an r-direction of said cylindrical coordinate system, said r-coils being wound on said yoke next to said second pair of coils, and being connected to a current supply which is separate from a current supply for said second pair of coils.

6. An X-ray tube as claimed in claim 1 wherein said magnet system comprises a quadrupole system for shaping said electrons into an electron beam.

7. An X-ray tube as claimed in claim 6 wherein said magnet system further comprises four quadrature coils respectively wound on said four pole projections for generating a quadrupole field which interacts with said electrons.

* * * * *